(12) United States Patent
Arai et al.

(10) Patent No.: US 10,111,858 B2
(45) Date of Patent: Oct. 30, 2018

(54) PHARMACEUTICAL FOR PROPHYLAXIS OR TREATMENT OF HYPERTENSION

(71) Applicant: Daiichi Sankyo Company, Limited, Chuo-ku, Tokyo (JP)

(72) Inventors: Kiyoshi Arai, Tokyo (JP); Tsuyoshi Homma, Tokyo (JP); Makoto Mizuno, Chiba (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 15/723,097

(22) Filed: Oct. 2, 2017

(65) Prior Publication Data
US 2018/0036281 A1  Feb. 8, 2018

Related U.S. Application Data

(60) Division of application No. 14/996,064, filed on Jan. 14, 2016, which is a continuation of application No. PCT/JP2014/069135, filed on Jul. 18, 2014.

(30) Foreign Application Priority Data

Jul. 23, 2013 (JP) .................................. 2013-152343

(51) Int. Cl.
| | |
|---|---|
| *A61K 31/40* | (2006.01) |
| *A61K 9/20* | (2006.01) |
| *A61K 31/4178* | (2006.01) |
| *A61K 31/4422* | (2006.01) |
| *A61K 31/549* | (2006.01) |
| *A61K 45/00* | (2006.01) |

(52) U.S. Cl.
CPC ............ *A61K 31/40* (2013.01); *A61K 9/2054* (2013.01); *A61K 31/4178* (2013.01); *A61K 31/4422* (2013.01); *A61K 31/549* (2013.01); *A61K 45/00* (2013.01)

(58) Field of Classification Search
None
See application file for complete search history.

(56) References Cited

U.S. PATENT DOCUMENTS

| | | | |
|---|---|---|---|
| 3,025,292 | A | 3/1962 | Jones et al. |
| 4,572,909 | A | 2/1986 | Campbell et al. |
| 5,616,599 | A | 4/1997 | Yanagisawa et al. |
| 8,524,918 | B2 | 9/2013 | Aoki et al. |
| 2005/0222137 | A1 | 10/2005 | Shetty et al. |

FOREIGN PATENT DOCUMENTS

| | | |
|---|---|---|
| EP | 2 133 330 A1 | 12/2009 |
| JP | 2005-533023 A | 11/2005 |
| JP | 2008-524136 A | 7/2008 |
| JP | 2010-111657 A | 5/2010 |
| WO | 2006/012642 A1 | 2/2006 |
| WO | 2006/063737 A2 | 6/2006 |
| WO | 2008/056907 A1 | 3/2008 |
| WO | 2008/126831 A1 | 10/2008 |

OTHER PUBLICATIONS

Van Buren et al., Hypertension in Diabetic Nephropathy: Epidemiology, Mechanisms, and Management., 2011, Adv Chronic Kidney Dis., 18(1), pp. 28-41 (Year: 2011).*
Extended European Search Report dated Feb. 24, 2017, issued in European Application No. 14830125.2, filed Jul. 18, 2014, 8 pages.
Fukuda, S., and A. Sato, "Aldosterone Breakthrough, and Potential of Mineralocorticoid Receptor Antagonists," Journal of Blood Pressure 20(1):43-48, Jan. 2013.
Gupta, V., "Mineralocorticoid Hypertension," Indian Journal of Endocrinology and Metabolism 15(Suppl. 4):S298-S312, Oct. 2011.
Horiuchi, M., "Protective Effects of Azelnidipine and Their Enhancement by the Combination With Angiotensin II Type 1 Receptor Blockers," Progress in Medicine 24(11):2682-2687, Nov. 2004.
International Preliminary Report on Patentability dated Jan. 26, 2016, issued in corresponding International Application No. PCT/JP2014/069135, filed Jul. 18, 2014, 12 pages.
International Search Report dated Nov. 4, 2014, issued in corresponding International Application No. PCT/JP2014/069135, filed Jul. 18, 2014, 7 pages.
Joh, R., and H. Shibata, "3. Anti-Aldosterone Drugs, and Potassium Sparing Diuretics," Modern Physician 31(6):725-730, Jun. 2011.
Julius, S., "Amlodipine in Hypertension: An Overview of the Clinical Dossier," Journal of Cardiovascular Pharmacology 12(Suppl. 7):S27-S33, 1988.
Messerli, F.H., et al., "Antihypertensive Efficacy of Hydrochlorothiazide as Evaluated by Ambulatory Blood Pressure Monitoring," Journal of the American College of Cardiology 52(5):594-600, Feb. 2011.
Mizuno, M., "Research Strategy 3 for Cardiovascular Disease Therapeutic Drugs: Combination Therapy With Antihypertensive Drugs: Organ Protective Effect by Combined Use of ARB and CCB," Folia Pharmacologica Japonica 139(6):246-250, Jun. 2012.
Ohno, Y., and H Suzuki, "New Drug Profile No. 2: ARB-Diuretic Combination Drug," Pharmaceuticals Monthly 51(12):1879-1883, Nov. 2009.
Scott, L.J., and P.L. McCormack, "Olmesartan Medoxomil: A Review of Its Use in the Management of Hypertension," Drugs 68(9):1239-1272, Jun. 2008.
Shibata, H., and H. Ito, "1. Mineralocorticoid Receptor-Associated Hypertension," Annual Review Diabetology, Metabolomics, and Endocrinology, III. Endocrinology, B. Developments in the Clinic 2013:185-192, Jan. 2013.
Notice of Reasons for Rejection dated Feb. 28, 2018, issued in corresponding Japanese Application No. 2015-528260, filed Jul. 18, 2014, 10 pages.
Suzuki, Y., et al., "Pharmacological Studies on Diuretics (6) Activities of Various Diuretics on Experimental Nephrotic Rats," Folia Pharmacol. Japon. 69:739-748, Sep. 1973.

* cited by examiner

*Primary Examiner* — Kortney L. Klinkel
*Assistant Examiner* — Tori Strong
(74) *Attorney, Agent, or Firm* — Christensen O'Connor Johnson Kindness PLLC

(57) ABSTRACT

A pharmaceutical for the prophylaxis or treatment of hypertension or a disease derived from hypertension. The pharmaceutical is characterized by comprising (i) a specific mineralocorticoid receptor antagonist and (ii) one or more components selected from the following components (A) to (C), for administration simultaneously or separately at a time interval: (A) an angiotensin II receptor antagonist, (B) a calcium antagonist, and (C) a diuretic.

12 Claims, No Drawings

PHARMACEUTICAL FOR PROPHYLAXIS OR TREATMENT OF HYPERTENSION

CROSS REFERENCES TO RELATED APPLICATIONS

This application is a division of U.S. application Ser. No. 14/996,064, filed Jan. 14, 2016, which is a continuation of PCT/JP2014/069135, filed Jul. 18, 2014, which claims priority to Japanese Application No. 2013-152343, filed Jul. 23, 2013. Each application is incorporated herein by reference in its entirety.

TECHNICAL FIELD

The present invention relates to a pharmaceutical for the prophylaxis or treatment of hypertension, a heart disease [angina pectoris, myocardial infarction, arrhythmia (including sudden death), heart failure, or cardiac hypertrophy], a kidney disease (diabetic nephropathy, glomerulonephritis, or nephrosclerosis), a cerebrovascular disease (cerebral infarction or intracerebral hemorrhage), or a vascular disorder (arteriosclerosis, restenosis after PTCA, or peripheral circulatory disturbance).

BACKGROUND ART

At present, angiotensin II receptor antagonists and calcium antagonists are widely used as pharmaceuticals for the treatment or prophylaxis of hypertension, a heart disease, or the like.

Mineralocorticoid receptors (MR) (aldosterone receptors) are known to play an important role in regulating electrolyte balance and blood pressure in the body, and MR antagonists having a steroidal structure such as spironolactone and eplerenone are known to be useful for the treatment of hypertension and heart failure.

Angiotensin II receptor antagonists which are renin-angiotensin system inhibitors are particularly effective in renin-dependent hypertension and exhibit a protective activity against cardiovascular disorders and kidney disorders. Further, calcium antagonists antagonize (inhibit) the function of calcium channels so as to have a natriuretic activity in addition to a vasodilatory activity, and are therefore effective also in fluid retention (renin-independent) hypertension.

Accordingly, it is expected that by using an MR antagonist and an angiotensin II receptor antagonist or a calcium antagonist in combination, multiple causes of high blood pressure can be suppressed simultaneously, and a stable and sufficient therapeutic or prophylactic effect on hypertension is exhibited regardless of the causes of the disease.

Further, also diuretics are widely used as pharmaceuticals for the treatment or prophylaxis of hypertension, a heart disease, or the like. Diuretics are effective in the treatment of hypertension because of their diuretic effect. Therefore, it is expected that by using an MR antagonist and a diuretic in combination, multiple causes of high blood pressure can be suppressed simultaneously because of the diuretic activity of the diuretic, and a stable and sufficient therapeutic or prophylactic effect on hypertension is exhibited regardless of the causes of the disease.

1-(2-Hydroxyethyl)-4-methyl-N-[4-(methylsulfonyl)phenyl]-5-[2-(trifluoromethyl)phenyl]-1H-pyrrole-3-carboxamide (hereinafter referred to as "compound (I)") is disclosed in PTL 1 and PTL 2, and is known to be useful for treating hypertension, diabetic nephropathy, and the like.

(5-Methyl-2-oxo-1,3-dioxolan-4-yl)methyl 4-(1-hydroxy-1-methylethyl)-2-propyl-1-[2'-(1H-tetrazol-5-yl) biphenyl-4-ylmethyl]imidazole-5-carboxylate (hereinafter referred to as "olmesartan medoxomil") is an angiotensin II receptor antagonist, and is known to be useful as a pharmaceutical for treatment or the prophylaxis of hypertension, a heart disease, and the like (PTL 3).

Olmesartan medoxomil is commercially available as Olmetec (registered trademark) tablet or Benicar®, each of which contains olmesartan medoxomil as an active ingredient in an amount of 5 mg, 10 mg, 20 mg, or 40 mg, and further contains low-substituted hydroxypropyl cellulose, hydroxypropyl cellulose, crystalline cellulose, lactose, and magnesium stearate as additives.

Further, 3-ethyl-5-methyl-(±)-2-[(2-aminoethoxy) methyl]-4-(2-chloro phenyl)-1,4-dihydro-6-methylpyridine-3,5-dicarboxylate (hereinafter referred to as "amlodipine") is a known compound as an excellent calcium antagonist and is useful as a pharmaceutical for the treatment or prophylaxis of hypertension, a heart disease, and the like (PTL 4)

Amlodipine is commercially available as Norvasc (registered trademark) tablets, which contain amlodipine besylate as an active ingredient in an amount of 3.47 mg or 6.93 mg (2.5 mg or 5 mg in terms of amlodipine) and further contains crystalline cellulose, anhydrous calcium hydrogen phosphate, carboxymethyl starch sodium, magnesium stearate, hydroxypropyl methyl cellulose, titanium oxide, talc, and carnauba wax as additives. Further, 6-chloro-3,4-dihydro-2H-1,2,4-benzothiadiazine-7-sulfonamide 1,1-dioxide (hereinafter referred to as "hydrochlorothiazide") is a known compound as an excellent thiazide-based diuretic and is described in, for example, PTL 5, and the like.

CITATION LIST

Patent Literature

PTL 1: WO 2006/012642 (US Patent Publication No. US2008-0234270)

PTL 2: WO 2008/056907 (US Patent Publication No. US2010-0093826)

PTL 3: Japanese Patent No. 2082519 (U.S. Pat. No. 5,616,599)

PTL 4: Japanese Patent No. 1401088 (U.S. Pat. No. 4,572,909)

PTL 5: U.S. Pat. No. 3,025,292

SUMMARY OF INVENTION

Technical Problem

An object of the present invention is to provide a pharmaceutical for the prophylaxis or treatment of hypertension or a disease derived from hypertension, more specifically, to provide a pharmaceutical for the prophylaxis and/or treatment of hypertension, a heart disease [angina pectoris, myocardial infarction, arrhythmia (including sudden death), heart failure, or cardiac hypertrophy], a kidney disease (diabetic nephropathy, glomerulonephritis, or nephrosclerosis), a cerebrovascular disease (cerebral infarction or intracerebral hemorrhage), or a vascular disorder (arteriosclerosis, restenosis after PTCA, or peripheral circulatory disturbance) (particularly a pharmaceutical for the prophylaxis or treatment of hypertension).

Solution to Problem

As a result of intensive studies to achieve the above object, the present inventors found that by combining a specific MR antagonist with an angiotensin II receptor antagonist, a calcium antagonist, or a diuretic, an excellent blood pressure lowering activity is exhibited. Further, the present inventors found that such a pharmaceutical is extremely effective in the prophylaxis and/or treatment of hypertension, a heart disease [angina pectoris, myocardial infarction, arrhythmia (including sudden death), heart failure, or cardiac hypertrophy], a kidney disease (diabetic nephropathy, glomerulonephritis, or nephrosclerosis), a cerebrovascular disease (cerebral infarction or intracerebral hemorrhage), or a vascular disorder (arteriosclerosis, restenosis after PTCA, or peripheral circulatory disturbance). The present invention has been completed based on the above findings.

That is, the present invention provides the following (1) to (13).

(1) A pharmaceutical for the prophylaxis or treatment of hypertension or a disease derived from hypertension, characterized by comprising (i) a mineralocorticoid receptor antagonist which contains a substance selected from the group consisting of a compound represented by the following formula (I):

[Chem. 1]

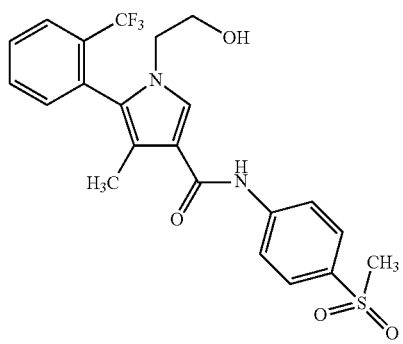

(I)

and an atropisomer thereof, and a pharmacologically acceptable salt thereof, and (ii) one or more components selected from the following components (A) to (C), for administration simultaneously or separately at a time interval:

(A) one or more angiotensin II receptor antagonists;

(B) one or more calcium antagonists comprising a substance selected from the group consisting of a 1,4-dihydropyridine-based compound and a pharmacologically acceptable salt thereof; and (C) one or more diuretics.

(2) A pharmaceutical for the prophylaxis or treatment of a disease selected from the group consisting of hypertension, a heart disease, angina pectoris, myocardial infarction, arrhythmia, sudden death, heart failure, cardiac hypertrophy, a kidney disease, diabetic nephropathy, glomerulonephritis, nephrosclerosis, a cerebrovascular disease, cerebral infarction, intracerebral hemorrhage, and a vascular disorder (arteriosclerosis, restenosis after PTCA, or peripheral circulatory disturbance), comprising one or more components selected from component (A), component (B), and component (C), and the mineralocorticoid receptor antagonist according to the above (1) as active ingredients.

(2-1) A pharmaceutical for the prophylaxis or treatment of hypertension and/or diabetic nephropathy, comprising one or more components selected from component (A), component (B), and component (C), and the mineralocorticoid receptor antagonist according to the above (1) as active ingredients.

(2-2) A pharmaceutical for treating hypertension, comprising one or more components selected from component (A), component (B), and component (C), and the mineralocorticoid receptor antagonist according to the above (1) as active ingredients.

(2-3) A pharmaceutical for treating diabetic nephropathy, containing one or more components selected from a component (A), a component (B), and a component (C), and the mineralocorticoid receptor antagonist according to the above (1) as active ingredients.

(3) The pharmaceutical according to the above (1) or (2), wherein the pharmaceutical is in the form of a pharmaceutical composition.

(4) The pharmaceutical according to any one of the above (1) to (3), wherein the angiotensin II receptor antagonist is (5-methyl-2-oxo-1,3-dioxolan-4-yl)methyl 4-(1-hydroxy-1-methylethyl)-2-propyl-1-[2'-(1H-tetrazol-5-yl)biphenyl-4-ylmethyl]imidazole-5-carboxylate.

(5) The pharmaceutical according to any one of the above (1) to (4), wherein the calcium antagonist is a calcium antagonist selected from the group consisting of azelnidipine, amlodipine, benidipine, nitrendipine, manidipine, nicardipine, nifedipine, nisoldipine, cilnidipine, lercanidipine, niguldipine, nimodipine, aranidipine, efonidipine, barnidipine, felodipine, clevidipine, lacidipine, and nilvadipine.

(6) The pharmaceutical according to any one of the above (1) to (4), wherein the calcium antagonist is amlodipine.

(7) The pharmaceutical according to any one of the above (1) to (6), wherein the diuretic is a diuretic selected from the group consisting of hydrochlorothiazide, methyclothiazide, benzylhydrochlorothiazide, trichloromethiazide, cyclopenthiazide, polythiazide, ethiazide, cyclothiazide, bendroflumethiazide, and hydroflumethiazide.

(8) The pharmaceutical according to any one of the above (1) to (6), wherein the diuretic is hydrochlorothiazide.

(9) The pharmaceutical according to the above (1), wherein the mineralocorticoid receptor antagonist is (S)-1-(2-hydroxyethyl)-4-methyl-N-[4-(methylsulfonyl)phenyl]-5-[2-(trifluoromethyl)phenyl]-1H-pyrrole-3-carboxamide represented by the following formula (Ia):

[Chem. 2]

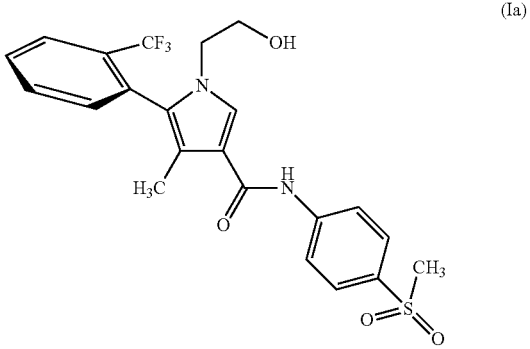

(Ia)

and the calcium antagonist is amlodipine.

(10) The pharmaceutical according to any one of the above (1) to (9), wherein the pharmaceutical is formulated as a single preparation.

(11) A pharmaceutical comprising a substance selected from the group consisting of compound (I), an atropisomer thereof, and a pharmacologically acceptable salt thereof for use in combination with one or more components selected from the following components (A) to (C):

(A) one or more angiotensin II receptor antagonists;
(B) one or more calcium antagonists comprising a substance selected from the group consisting of a 1,4-dihydropyridine-based compound and a pharmacologically acceptable salt thereof; and
(C) one or more diuretics.

(12) A pharmaceutical which comprises a substance selected from the group consisting of a compound (I), an atropisomer thereof, and a pharmacologically acceptable salt thereof, and enhances the activity of components (A) to (C) by comprising one or more components selected from the following components (A) to (C) in combination:

(A) one or more angiotensin II receptor antagonists;
(B) one or more calcium antagonists comprising a substance selected from the group consisting of a 1,4-dihydropyridine-based compound and a pharmacologically acceptable salt thereof; and
(C) one or more diuretics.

(13) The pharmaceutical according to the above (11) or (12), wherein the compound (I) is (S)-1-(2-hydroxyethyl)-4-methyl-N-[4-(methylsulfonyl)phenyl]-5-[2-(trifluoromethyl)phenyl]-1H-pyrrole-3-carboxamide.

Further, according to the present invention, use of a mineralocorticoid receptor antagonist which comprises a substance selected from the group consisting of a compound represented by the above formula (I), an atropisomer thereof, and a pharmacologically acceptable salt thereof, and component (A), component (B), or component (C) for producing the pharmaceutical; and a prophylaxis or treatment method (particularly a treatment method) for a disease, including administering effective amounts of a mineralocorticoid receptor antagonist which comprises a substance selected from the group consisting of a compound represented by the above formula (I), an atropisomer thereof, and a pharmacologically acceptable salt thereof, and component (A), component (B) or component (C) to a warm-blooded animal (particularly a human being) are provided.

According to preferred embodiments of the respective inventions described above, the pharmaceutical is provided as a pharmaceutical composition comprising a mineralocorticoid receptor antagonist which comprises a substance selected from the group consisting of a compound represented by the above formula (I), an atropisomer thereof, and a pharmacologically acceptable salt thereof, and component (A), component (B) or component (C) as active ingredients, and this pharmaceutical composition may comprise one or more pharmaceutical additives.

Advantageous Effects of Invention

A pharmaceutical comprising an angiotensin II receptor antagonist, a calcium antagonist, or a diuretic, and an MR antagonist as active ingredients of the present invention has an excellent blood pressure lowering activity and also has low toxicity, and therefore is useful as a pharmaceutical {preferably a prophylactic agent or a therapeutic agent (particularly a therapeutic agent) for hypertension, a heart disease [angina pectoris, myocardial infarction, arrhythmia (including sudden death), heart failure, or cardiac hypertrophy], a kidney disease (diabetic nephropathy, glomerulonephritis, or nephrosclerosis), a cerebrovascular disease (cerebral infarction or intracerebral hemorrhage), or a vascular disorder (arteriosclerosis, restenosis after PTCA, or peripheral circulatory disturbance), more preferably a prophylactic agent or a therapeutic agent (particularly a therapeutic agent) for hypertension or a heart disease, and particularly preferably a prophylactic agent or a therapeutic agent (particularly a therapeutic agent) for hypertension}. Further, the pharmaceutical is preferably used for a warm-blooded animal, and more preferably used for a human being.

DESCRIPTION OF EMBODIMENTS

The pharmaceutical of the present invention is characterized by comprising a mineralocorticoid receptor antagonist which comprises a substance selected from the group consisting of a compound represented by the above formula (I), an atropisomer thereof, and a pharmacologically acceptable salt thereof, and (A) one or more angiotensin II receptor antagonists;
(B) one or more calcium antagonists comprising a substance selected from the group consisting of a 1,4-dihydropyridine-based compound and a pharmacologically acceptable salt thereof; or
(C) one or more diuretics as active ingredients.

The compound represented by the above formula (I), an atropisomer thereof, or a pharmacologically acceptable salt thereof serving as an active ingredient of the present invention is known, and can be produced by, for example, the method described in WO 2006/012642 (US Patent Publication No. US2008-0234270), WO 2008/056907 (US Patent Publication No. US2010-0093826), or the like. The compound (I) or an atropisomer thereof is preferably the following atropisomer compound (Ia).

[Chem. 3]

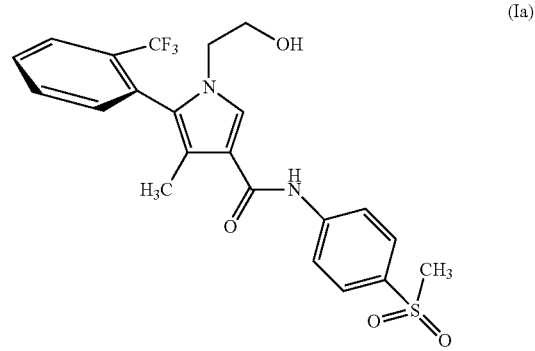

(Ia)

As a substance selected from the compound represented by the above formula (I) or an atropisomer thereof, a hydrate or a solvate can also be used. As the compound represented by the above formula (I), an atropisomer in pure form or an arbitrary mixture of atropisomers can also be used.

Examples of the angiotensin II receptor antagonist to be used as the component (A) include biphenyl tetrazole compounds such as olmesartan medoxomil, olmesartan cilexetil, losartan, candesartan cilexetil, valsartan, and irbesartan, biphenyl carboxylic acid compounds such as telmisartan, eprosartan, and azilsartan, and the angiotensin II receptor antagonist is preferably a biphenyl tetrazole compound, more preferably olmesartan medoxomil, losartan, candesartan cilexetil, valsartan, or irbesartan, particularly preferably olmesartan medoxomil, losartan, or candesartan cilexetil, and most preferably olmesartan medoxomil.

Olmesartan medoxomil is described in JP-A-5-78328, U.S. Pat. No. 5,616,599, and the like, and its chemical name is (5-methyl-2-oxo-1,3-dioxolan-4-yl)methyl 4-(1-hydroxy-1-methylethyl)-2-propyl-1-[2'-(1H-tetrazol-5-yl)biphenyl-4-ylmethyl]imidazole-5-carboxylate, and olmesartan medoxomil as used herein encompasses a pharmacologically acceptable salt thereof.

Losartan (DUP-753) is described in JP-A-63-23868, U.S. Pat. No. 5,138,069, and the like, and its chemical name is 2-butyl-4-chloro-1-[2'-(1H-tetrazol-5-yl)biphenyl-4-ylmethyl]-1H-imidazole-5-methanol, and losartan as used herein encompasses a pharmacologically acceptable salt thereof (losartan potassium salt or the like).

Candesartan cilexetil is described in JP-A-4-364171, EP-459136, U.S. Pat. No. 5,354,766, and the like, and its chemical name is 1-(cyclohexyloxycarbonyloxy)ethyl-2-ethoxy-1-[2'-(1H-tetrazol-5-yl)biphenyl-4-ylmethyl]-1H-benzimidazole-7-carboxylate, and candesartan cilexetil as used herein encompasses a pharmacologically acceptable salt thereof.

Valsartan (CGP-48933) is described in JP-A-4-159718, EP-433983, and the like, and its chemical name is (S)—N-valeryl-N-[2'-(1H-tetrazol-5-yl)biphenyl-4-ylmethyl) valine, and valsartan as used herein encompasses a pharmacologically acceptable ester thereof or a pharmacologically acceptable salt thereof.

Irbesartan (SR-47436) is described in JP-T-4-506222, WO 91-14679, and the like, and its chemical name is 2-N-butyl-4-spirocyclopentane-1-[2'-(tetrazol-5-yl)biphenyl-4-ylmethyl]-2-imidazoline-5-one, and irbesartan as used herein encompasses a pharmacologically acceptable salt thereof.

Eprosartan (SKB-108566) is described in U.S. Pat. No. 5,185,351 and the like, and its chemical name is 3-[1-(4-carboxyphenylmethyl)-2-n-butyl-imidazol-5-yl]-2-thienylmethyl-2-propenoic acid, and eprosartan as used herein encompasses a carboxylic acid derivative thereof, a pharmacologically acceptable ester of a carboxylic acid derivative, or a pharmacologically acceptable salt thereof (eprosartan mesylate or the like).

Telmisartan (BIBR-277) is described in U.S. Pat. No. 5,591,762 and the like, and its chemical name is 4'-[[4-methyl-6-(1-methyl-2-benzimidazolyl)-2-propyl-1-benzimidazolyl]methyl]-2-biphenylcarboxylic acid, and telmisartan as used herein encompasses a carboxylic acid derivative thereof, a pharmacologically acceptable ester of a carboxylic acid derivative, or a pharmacologically acceptable salt thereof.

Azilsartan is described in JP-A-05-271228, U.S. Pat. No. 5,243,054, and the like, and its chemical name is 2-ethoxy-1{[2'-(5-oxo-4,5-dihydro-1,2,4-oxadiazol-3-yl)biphenyl-4-yl]methyl}-1H-benzo[d]imidazole-7-carboxylic acid.

Further, in the case where the above compounds have an asymmetric carbon, the angiotensin II receptor antagonist of the present invention also encompasses optical isomers and mixtures of isomers thereof. Further, it also encompasses hydrates of the compounds.

The calcium antagonist containing a 1,4-dihydropyridine-based compound to be used as the component (B) is a calcium antagonist characterized by having a 1,4-dihydropyridine partial structure or a partial structure chemically equivalent thereto in the molecule. As calcium antagonists containing a 1,4-dihydropyridine-based compound, various agents have been proposed and are actually used in clinical practice, and therefore, those skilled in the art can select a suitable agent exhibiting the effect of the present invention. As a calcium antagonist containing a 1,4-dihydropyridine-based compound, for example, azelnidipine, amlodipine, benidipine, nitrendipine, manidipine, nicardipine, nifedipine, nisoldipine, cilnidipine, lercanidipine, niguldipine, nimodipine, aranidipine, efonidipine, barnidipine, felodipine, clevidipine, lacidipine, nilvadipine, or the like can be used, however, the calcium antagonist is not limited thereto.

The type of the pharmacologically acceptable salt of the 1,4-dihydropyridine-based compound is not particularly limited and can be suitably selected by those skilled in the art. The pharmacologically acceptable salt may be either an acid addition salt or a base addition salt. Examples thereof include metal salts including alkali metal salts such as sodium salts, potassium salts, and lithium salts, alkaline earth metal salts such as calcium salts and magnesium salts, aluminum salts, iron salts, zinc salts, copper salts, nickel salts, and cobalt salts; base addition salts such as amine salts including inorganic salts such as ammonium salts and organic salts such as t-octyl amine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethyl ammonium salts, and tris(hydroxymethyl)aminomethane salts; mineral acid salts such as hydrofluorides, hydrochlorides, hydrobromides, hydroiodides, nitrates, perchlorates, sulfates, and phosphates; sulfonates such as methanesulfonates, trifluoromethanesulfonates, ethanesulfonates, benzenesulfonates, and p-toluenesulfonates; carboxylates such as besylates, fumarates, succinates, citrates, tartrates, oxalates, and maleates; and amino acid salts such as glutamates and aspartates, however, the salt is not limited thereto.

As the calcium antagonist containing a 1,4-dihydropyridine-based compound, a hydrate or a solvate of the abovementioned compound or a pharmacologically acceptable salt thereof may be used. Further, the calcium antagonist containing a 1,4-dihydropyridine-based compound sometimes has one or more asymmetric carbon atoms in the molecule, however, an optical isomer or a stereoisomer such as a diastereoisomer in pure form based on the asymmetric carbon, or an arbitrary mixture of stereoisomers or a racemic mixture, or the like can also be used as the component (B). As the component (B), (±)-2-amino-1,4-dihydro-6-methyl-4-(3-nitrophenyl)-3,5-pyridinedicarboxylic acid 3-(1-diphenylmethylazetidin-3-yl)ester 5-isopropyl ester is preferred.

The calcium antagonist containing a 1,4-dihydropyridine-based compound is more preferably amlodipine, and can be easily produced according to the method described in Japanese Patent No. 1401088 (U.S. Pat. No. 4,572,909) or the like. Amlodipine can form pharmacologically acceptable salts, and the present invention also encompasses these salts. The pharmacologically acceptable salt may be either an acid addition salt or a base addition salt. Examples thereof include besylates, hydrochlorides, hydrobromides, fumarates, citrates, tartrates, maleates, camsilates, lactates, mesylates, nicotinates, and gluconates. The salt is not limited thereto, but is preferably a besylate.

The diuretic to be used as the component (C) is a known compound, and is described in, for example, U.S. Pat. No. 2,554,816, U.S. Pat. No. 2,980,679, U.S. Pat. No. 2,783,241, UK Patent No. 795,174, U.S. Pat. No. 2,835,702, UK Patent No. 851,287, U.S. Pat. No. 3,356,692, U.S. Pat. No. 3,055,904, U.S. Pat. No. 2,976,289, U.S. Pat. No. 3,058,882, Pharmacometrics, vol. 21, 607 (1982), U.S. Pat. No. 3,183,243, U.S. Pat. No. 3,360,518, U.S. Pat. No. 3,567,777, U.S. Pat. No. 3,634,583, U.S. Pat. No. 3,025,292, U.S. Pat. No.

3,108,097, U.S. Pat. No. 3,009,911, U.S. Pat. No. 3,265,573, U.S. Pat. No. 3,254,076, U.S. Pat. No. 3,255,241, U.S. Pat. No. 3,758,506, U.S. Pat. No. 3,163,645, and the like, and can be a sulfonamide-based compound such as acetazolamide, methazolamide, ethoxzolamide, clofenamide, dichlorphenamide, disuflamide, mefruside, chlorthalidone, quinethazone, furosemide, clopamide, tripamide, indapamide, clorexolone, metolazone, xipamide, bumetanide, piretanide, or X-54; a thiazide-based compound such as hydrochlorothiazide, methylclothiazide, benzylhydrochlorothiazide, trichloromethiazide, cyclopenthiazide, polythiazide, ethiazide, cyclothiazide, bendroflumethiazide, or hydroflumethiazide; a phenoxyacetic acid-based compound such as ethacrynic acid, tienilic acid, indacrinone, or quincarbate; triamterene; amiloride; spironolactone; potassium canrenoate; torasemide; MK-447; or traxanox sodium, and is preferably a thiazide-based compound, and more preferably hydrochlorothiazide.

The chemical name of hydrochlorothiazide is 6-chloro-3,4-dihydro-2H-1,2,4-benzothiadiazine-7-sulfonamide 1,1-dioxide, and hydrochlorothiazide as used herein encompasses a pharmacologically acceptable salt thereof, and the salt can be, for example, a hydrogen halide salt such as a hydrofluoride, a hydrochloride, a hydrobromide, or a hydroiodide; a nitrate; a perchlorate; a sulfate; a phosphate; a C1-C4 alkane sulfonate which may be substituted with halogen such as a methanesulfonate, a trifluoromethanesulfonate, or an ethanesulfonate; a C6-C10 aryl sulfonate which may be substituted with C1-C4 alkyl such as a benzenesulfonate or a p-toluenesulfonate; a C1-C6 fatty acid salt such as acetate, malate, a fumarate, a succinate, a citrate, a tartrate, an oxalate, or a maleate; or an amino acid salt such as a glycine salt, a lysine salt, an arginine salt, an ornithine salt, a glutamate, or an aspartate, and is preferably a hydrochloride, a nitrate, a sulfate, or a phosphate, and particularly preferably a hydrochloride.

Further, in the case where the above compounds have an asymmetric carbon, the diuretic of the present invention also encompasses optical isomers and mixtures of isomers thereof. Further, it also encompasses hydrates of the compounds.

In the invention, the phrase administered "simultaneously" is not particularly limited as long as it is an administration form capable of performing administration at substantially the same time, however, it is preferred to perform administration as a single composition.

In the invention, the phrase administered "separately at a time interval" is not particularly limited as long as it is an administration form capable of performing administration separately at different times, however, for example, it refers to that first, an MR antagonist is administered, and then, after a predetermined time, a calcium antagonist is administered, or first, a calcium antagonist or a diuretic is administered, and then, after a predetermined time, an MR antagonist is administered in the same manner as described above.

A pharmaceutical composition for administering simultaneously or separately at a time interval the MR antagonist and the angiotensin II receptor antagonist, the calcium antagonist, or the diuretic of the present invention can further lower the blood pressure by allowing the MR antagonist and component (A), component (B), or component (C) to act as specifically described in the Examples of this description. Based on the activity described above, the pharmaceutical of the present invention can be used for the prophylaxis or treatment (particularly treatment) of hypertension, a heart disease [angina pectoris, myocardial infarction, arrhythmia (including sudden death), heart failure, or cardiac hypertrophy], a kidney disease (diabetic nephropathy, glomerulonephritis, or nephrosclerosis), a cerebrovascular disease (cerebral infarction or intracerebral hemorrhage), or a vascular disorder (arteriosclerosis, restenosis after PTCA, or peripheral circulatory disturbance). Incidentally, by using the MR antagonist and the angiotensin II receptor antagonist, the calcium antagonist, or the diuretic of the present invention in combination, a more excellent effect is exhibited as compared with the case where each agent is administered singly.

The MR antagonist and the angiotensin II receptor antagonist, the calcium antagonist, or the diuretic serving as the active ingredients of the pharmaceutical composition of the present invention can be prepared in the form of separate unit dosage forms each containing a single agent alone, or can be prepared physically in the form of one unit dosage form by mixing these agents.

In the case where the pharmaceutical composition of the present invention is used as a prophylactic agent or a therapeutic agent for any of the above-mentioned diseases, the MR antagonist and the angiotensin II receptor antagonist, the calcium antagonist, or the diuretic serving as the active ingredients of the pharmaceutical composition of the present invention can be administered orally in the form of a tablet, a capsule, a granule, a powder, a syrup, or the like, or parenterally in the form of an injection, a suppository, or the like, which is produced according to a known method using the respective agents by themselves, or by using also a suitable pharmacologically acceptable additive such as an excipient, a lubricant, a binder, a disintegrant, an emulsifier, a stabilizer, a corrigent, or a diluent. Incidentally, the MR antagonist, and the components (A), (B), and (C) to be comprised in the pharmaceutical of the present invention are agents to be generally administered orally, and therefore, the pharmaceutical of the present invention is desirably administered orally.

Examples of the "excipient" to be used include organic excipients including sugar derivatives such as lactose, white soft sugar, glucose, mannitol, and sorbitol; starch derivatives such as corn starch, potato starch, pregelatinized starch, and dextrin; cellulose derivatives such as crystalline cellulose; gum arabic; dextran; and pullulan; and inorganic excipients including silicate derivatives such as light anhydrous silicic acid, synthetic aluminum silicate, calcium silicate, and magnesium metasilicate aluminate; phosphates such as calcium hydrogen phosphate; carbonates such as calcium carbonate; and sulfates such as calcium sulfate.

Examples of the "lubricant" to be used include stearic acid; stearic acid metal salts such as calcium stearate and magnesium stearate; talc; colloidal silica; waxes such as beeswax and spermaceti; boric acid; adipic acid; sulfates such as sodium sulfate; glycol; fumaric acid; sodium stearyl fumarate; sodium benzoate; D,L-leucine; lauryl sulfates such as sodium lauryl sulfate and magnesium lauryl sulfate; silicates such as anhydrous silicic acid and silicate hydrate; and the above-mentioned starch derivatives.

Examples of the "binder" to be used include hydroxypropyl cellulose, hydroxypropyl methyl cellulose, polyvinylpyrrolidone, macrogol, and compounds similar to the above-mentioned excipients Examples of the "disintegrant" to be used include cellulose derivatives such as low-substituted hydroxypropyl cellulose, carboxymethyl cellulose, calcium carboxymethyl cellulose, and internally crosslinked sodium carboxymethyl cellulose; cross-linked polyvinylpyrrolidone; and chemically modified starches and celluloses such as carboxymethyl starch and sodium carboxymethyl starch.

Examples of the "emulsifier" to be used include colloidal clays such as bentonite and Veegum; metal hydroxides such as magnesium hydroxide and aluminum hydroxide; anionic surfactants such as sodium lauryl sulfate and calcium stearate; cationic surfactants such as benzalkonium chloride; and nonionic surfactants such as polyoxyethylene alkyl ether, polyoxyethylene sorbitan fatty acid ester, and sucrose fatty acid ester.

Examples of the "stabilizer" to be used include p-hydroxybenzoate esters such as methyl paraben and propyl paraben; alcohols such as chlorobutanol, benzyl alcohol, and phenyl ethyl alcohol; benzalkonium chloride; phenols such as phenol and cresol; thimerosal; dehydroacetic acid; and sorbic acid.

Examples of the "corrigent" to be used include sweeteners such as sodium saccharin and aspartame; acidulants such as citric acid, malic acid, and tartaric acid; and flavors such as menthol, lemon, and orange flavors.

Examples of the "diluent" to be used include materials generally used as a diluent such as lactose, mannitol, glucose, sucrose, calcium sulfate, calcium phosphate, hydroxypropyl cellulose, microcrystalline cellulose, water, ethanol, polyethylene glycol, propylene glycol, glycerol, starch, polyvinylpyrrolidone, magnesium metasilicate aluminate, and mixtures thereof.

The doses of the mineralocorticoid receptor antagonist, the angiotensin II receptor antagonist, the calcium antagonist, and the diuretic serving as the active ingredients of the pharmaceutical composition of the present invention can vary depending on various conditions such as the activities of the respective agents, and the symptoms, age, body weight, etc. of a patient. The doses vary depending on the symptoms, age, etc., however, each agent can be administered at a dose of 0.1 mg (preferably 0.5 mg) as a lower limit and 1000 mg (preferably 500 mg) as an upper limit in the case of oral administration, and at a dose of 0.01 mg (preferably 0.05 mg) as a lower limit and 100 mg (preferably 50 mg) as an upper limit in the case of parenteral administration to a human adult 1 to 6 times per day depending on the symptoms, and the agents can be administered simultaneously or separately at a time interval.

Further, the ratio of the doses of the MR antagonist and the angiotensin II receptor antagonist, the calcium antagonist, or the diuretic serving as the active ingredients of the pharmaceutical composition of the present invention can also largely vary, but the weight ratio thereof can be in the range of 1:1-10000 to 10000:1-10000, preferably in the range of 1:1-1000 to 1000:1-1000, more preferably in the range of 1:1-100 to 100:1-100. Further, the doses in the case where the mineralocorticoid receptor antagonist serving as the active ingredient of the pharmaceutical composition of the present invention is (S)-1-(2-hydroxyethyl)-4-methyl-N-[4-(methylsulfonyl)phenyl]-5-[2-(trifluoromethyl)phenyl]-1H-pyrrole-3-carboxamide, the angiotensin II receptor antagonist is olmesartan medoxomil, the calcium antagonist is amlodipine, and the diuretic is hydrochlorothiazide can vary depending on various conditions such as the activities of the respective agents, and the symptoms, age, body weight, etc. of a patient, and therefore vary depending on the symptoms, age, etc., however, in the case of oral administration, (S)-1-(2-hydroxyethyl)-4-methyl-N-[4-(methylsulfonyl)phenyl]-5-[2-(trifluoromethyl)phenyl]-1H-pyrrole-3-carboxamide can be administered at a daily dose of 1.0 mg to 10 mg (preferably 2.5 mg to 5 mg), olmesartan medoxomil can be administered at a daily dose of 5 mg to 80 mg (preferably 10 mg to 40 mg), amlodipine can be administered at a daily dose (on the free form basis) of 2.5 mg to 20 mg (preferably 5 mg to 10 mg), and hydrochlorothiazide can be administered at a daily dose (on the free form basis) of 5 mg to 50 mg (preferably 12.5 mg to 25 mg) to a human adult 1 to 6 times per day (preferably once per day) depending on the symptoms.

Incidentally, in the case where the MR antagonist is used for the prophylaxis or treatment of hypertension in the present invention, the dose of the MR antagonist can be somewhat lower than in the case where it is used as a pressure lowering agent which is its original usage, and the dose thereof can be further decreased by the excellent effect of combined administration thereof with the angiotensin II receptor antagonist, the calcium antagonist, or the diuretic.

EXAMPLES

Hereinafter, the present invention will be described in further detail with reference to Examples and the like, however, the scope of the present invention is not limited thereto.

<Example 1> Test of Combined Administration of MR Antagonist and Angiotensin II Receptor Antagonist to Evaluate the Inhibitory Action on Blood Pressure Elevation Male Dahl rats (DIS/Eis [Dahl-Iwai S], SPF grade, supplier: Japan SLC, Inc., salt-sensitive hypertensive rats) at 7 weeks of age were divided into groups (6 rats per group).

In a normal group and a control group, 0.5% methyl cellulose solution was orally administered for 6 weeks, and in the other groups, a test substance was orally administered for 6 weeks. The test substance was suspended in 0.5% methyl cellulose solution and administered at a volume of 2 mL/kg. Additionally, in the groups other than the normal group, an 8% salt diet (FR-2 containing 8% NaCl, manufactured by Funabashi Farm Co., Ltd.) was given ad libitum from the start of administration of the test substance. The composition of the groups and the administered test substances [in parentheses] are as follows.

Group 1: normal group
Group 2: control group
Group 3: compound (Ia) administration group [compound (Ia) (1.0 mg/kg)]
Group 4: olmesartan medoxomil administration group [olmesartan medoxomil (10 mg/kg)]
Group 5: combined administration group [compound (Ia) (1.0 mg/kg)+olmesartan medoxomil (10 mg/kg)]

The results obtained by measuring systolic blood pressure using a noninvasive sphygmomanometer for rats and mice (BP-98A, Softron Co., Ltd.) during the trough period at the 6th week of administration of the test substance (on day 42 from the start of administration of the test substance) are shown in Table 1 (the values in the table represent mean±standard error).

TABLE 1

| Administration group | Systolic blood pressure (mmHg) |
|---|---|
| Group 1: normal group | 129 ± 5 |
| Group 2: control group | 219 ± 4 |
| Group 3: compound (Ia) administration group | 170 ± 4 |
| Group 4: olmesartan medoxomil administration group | 202 ± 8 |
| Group 5: combined administration group | 158 ± 3 |

With the combined administration of the MR antagonist and the angiotensin II receptor antagonist, an excellent pressure lowering action (inhibition of blood pressure elevation) was confirmed.

<Example 2> Test of Combined Administration of MR Antagonist and Calcium Antagonist to Evaluate the Inhibitory Action on Blood Pressure Elevation Male Dahl rats (DIS/Eis [Dahl-Iwai S], SPF grade, supplier: Japan SLC, Inc., salt-sensitive hypertensive rats) at 7 weeks of age were divided into groups (6 or 9 rats per group).

In a normal group and a control group, 0.5% methyl cellulose solution was orally administered for 6 weeks, and in the other groups, a test substance was orally administered for 6 weeks. The test substance was suspended in 0.5% methyl cellulose solution and administered at a volume of 2 mL/kg. Additionally, in the groups other than the normal group, an 8% salt diet (FR-2 containing 8% NaCl, manufactured by Funabashi Farm Co., Ltd.) was given ad libitum from the start of administration of the test substance. The composition of the groups, the administered test substances [ in parentheses], and the number of rats (n) per group are as follows.

Group 1: normal group n=6
Group 2: control group n=9
Group 3: compound (Ia) administration group [compound (Ia) (0.1 mg/kg)] n=6
Group 4: amlodipine administration group [amlodipine (1 mg/kg)] n=6
Group 5: combined administration group [compound (Ia) (0.1 mg/kg)+amlodipine (1 mg/kg)] n=6

The results obtained by measuring systolic blood pressure using a noninvasive sphygmomanometer for rats and mice (BP-98A, Softron Co., Ltd.) during the trough period at the 6th week of administration of the test substance (on day 41 from the start of administration of the test substance) are shown in Table 2 (the values in the table represent mean±standard error).

TABLE 2

| Administration group | Systolic blood pressure (mmHg) |
| --- | --- |
| Group 1: normal group | 138 ± 6 |
| Group 2: control group | 210 ± 2 |
| Group 3: compound (Ia) administration group | 207 ± 7 |
| Group 4: amlodipine administration group | 207 ± 5 |
| Group 5: combined administration group | 189 ± 9 |

With the combined administration of the MR antagonist and the calcium antagonist, an excellent pressure lowering action (inhibition of blood pressure elevation) was confirmed.

<Example 3> Test of Combined Administration of MR Antagonist and Diuretic to Evaluate the Inhibitory Action on Blood Pressure Elevation and Proteinuria Male Dahl rats (DIS/Eis [Dahl-Iwai S], SPF grade, supplier: Japan SLC, Inc., salt-sensitive hypertensive rats) at 7 weeks of age were divided into groups (6 or 9 rats per group).

In a normal group and a control group, 0.5% methyl cellulose solution was orally administered for 6 weeks, and in the other groups, a test substance was orally administered for 6 weeks. The test substance was suspended in 0.5% methyl cellulose solution and administered at a volume of 2 mL/kg. Additionally, in the groups other than the normal group, an 8% salt diet (FR-2 containing 8% NaCl, manufactured by Funabashi Farm Co., Ltd.) was given ad libitum from the start of administration of the test substance. The composition of the groups, the administered test substances [in the parentheses], and the number of rats (n) per group are as follows.

Group 1: normal group n=6
Group 2: control group n=9
Group 3: compound (Ia) administration group [compound (Ia) (0.3 mg/kg)] n=6
Group 4: hydrochlorothiazide administration group [hydrochlorothiazide (1 mg/kg)] n=6
Group 5: combined administration group [compound (Ia) (0.3 mg/kg)+hydrochlorothiazide (1 mg/kg)] n=6

Systolic blood pressure was measured by using a noninvasive sphygmomanometer for rats and mice (BP-98A, Softron Co., Ltd.) during the trough period at the 6th week of administration of the test substance (on day 40 from the start of administration of the test substance). In addition, on day 41 from the start of administration of the test substance, urine collection for 24-hour was performed using a metabolic cage (2100-R, Watanabe Isolator Systems Co., Ltd.), and the daily urinary protein excretion per body weight was calculated.

The results are shown in Table 3 (the values in the table represent mean±standard error).

TABLE 3

| Administration group | Systolic blood pressure (mmHg) | Daily urinary protein excretion (mg/kg/day) |
| --- | --- | --- |
| Group 1: normal group | 150 ± 3 | 87 ± 5 |
| Group 2: control group | 225 ± 6 | 447 ± 88 |
| Group 3: compound (Ia) administration group | 196 ± 7 | 190 ± 16 |
| Group 4: hydrochlorothiazide administration group | 212 ± 3 | 320 ± 65 |
| Group 5: combined administration group | 189 ± 3 | 167 ± 20 |

With the combined administration of the MR antagonist and the diuretic, an excellent pressure lowering action (inhibition of blood pressure elevation) and an excellent inhibitory action on proteinuria were confirmed.

<Preparation Example 1> Tablet (Fixed Dosage)

| | |
| --- | --- |
| Compound (Ia) | 5.00 mg |
| Amlodipine besylate | 13.89 mg |
| Pregelatinized starch | 105.00 mg |
| Crystalline cellulose | 147.41 mg |
| Carmellose sodium | 15.00 mg |
| Magnesium stearate | 1.20 mg |

A powder having the above formulation is mixed and tableted with a tableting machine, thereby forming a tablet (300 mg/tablet). This tablet can be sugar-coated as needed.

INDUSTRIAL APPLICABILITY

According to the present invention, a pharmaceutical for the prophylaxis or treatment of hypertension or a disease derived from hypertension is obtained. More specifically, a pharmaceutical for the prophylaxis and/or treatment of hypertension, a heart disease [angina pectoris, myocardial infarction, arrhythmia (including sudden death), heart failure, or cardiac hypertrophy], a kidney disease (diabetic nephropathy, glomerulonephritis, or nephrosclerosis), a cerebrovascular disease (cerebral infarction or intracerebral hemorrhage), or a vascular disorder (arteriosclerosis, restenosis after PTCA, or peripheral circulatory disturbance) is obtained.

The invention claimed is:

1. A method for the treatment of diabetic nephropathy, comprising administering to a subject in need thereof a therapeutically effective amount of a pharmaceutical comprising
   (i) a mineralocorticoid receptor antagonist represented by formula (I):

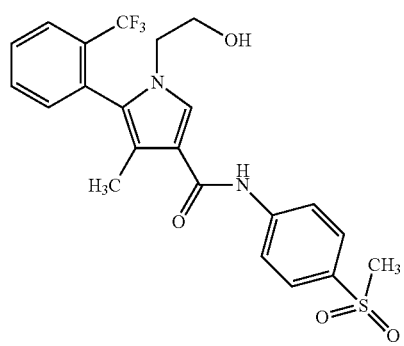

an atropisomer thereof, or a pharmacologically acceptable salt thereof, and
   (ii) (5-methyl-2-oxo-1,3-dioxolan-4-yl) methyl-4-(1-hydroxy-1-methylethyl)-2-propyl-1-[2'-(1H-tetrazol-5-yl)biphenyl-4-ylmethyl]imidazole-5-carboxylate, or a pharmacologically acceptable salt thereof.

2. The method according to claim 1, wherein the pharmaceutical is in the form of a pharmaceutical composition.

3. The method according to claim 1, wherein the mineralocorticoid receptor antagonist is (S)-1-(2-hydroxyethyl)-4-methyl-N-[4-(methylsulfonyl) phenyl]-5-[2-(trifluoromethyl)phenyl]-1H-pyrrole-3-carboxamide represented by formula (Ia):

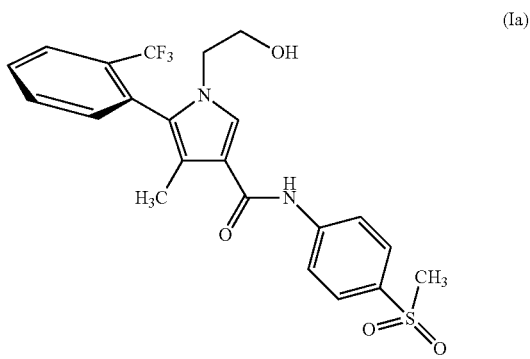

or a pharmacologically acceptable salt thereof.

4. The method according to claim 1, wherein the pharmaceutical is formulated as a single preparation.

5. The method according to claim 1, further comprising one or more calcium antagonists.

6. The method according to claim 5, wherein the one or more calcium antagonists are selected from the group consisting of a 1,4-dihydropyridine-based compound and a pharmacologically acceptable salt thereof.

7. The method according to claim 5, wherein the calcium antagonist is amlodipine.

8. The method according to claim 5, further comprising one or more diuretics.

9. The method according to claim 8, wherein the diuretic is hydrochlorothiazide.

10. The method according to claim 1, further comprising one or more diuretics.

11. The method according to claim 10, wherein the diuretic is hydrochlorothiazide.

12. The method according to claim 1, wherein the subject is a human.

* * * * *